United States Patent
Scott et al.

(10) Patent No.: US 9,700,376 B2
(45) Date of Patent: Jul. 11, 2017

(54) MULTI-JOINT FIXTURE SYSTEM

(71) Applicant: Surgical Concept Designs LLC, Hackensack, NJ (US)

(72) Inventors: Christopher P. Scott, Hackensack, NJ (US); Edward J. Laganis, Hoboken, NJ (US); Anthony J. LaRosa, Rockaway, NJ (US); Jason R. Cahayla, Saddleback, NJ (US)

(73) Assignee: Christopher P. Scott, Hackensack, NJ (US)

( * ) Notice: Subject to any disclaimer, the term of this patent is extended or adjusted under 35 U.S.C. 154(b) by 724 days.

(21) Appl. No.: 14/094,722

(22) Filed: Dec. 2, 2013

(65) Prior Publication Data

US 2014/0084761 A1    Mar. 27, 2014

Related U.S. Application Data

(62) Division of application No. 11/809,305, filed on May 31, 2007, now abandoned.

(Continued)

(51) Int. Cl.
| | |
|---|---|
| *A61B 19/00* | (2006.01) |
| *A61B 19/02* | (2006.01) |
| *A61B 17/02* | (2006.01) |
| *F16C 11/06* | (2006.01) |
| *F16C 11/10* | (2006.01) |

(Continued)

(52) U.S. Cl.
CPC .......... *A61B 19/0256* (2013.01); *A61B 17/02* (2013.01); *A61B 46/10* (2016.02); *A61B 46/23* (2016.02); *A61B 50/10* (2016.02); *A61B 50/13* (2016.02); *A61B 50/20* (2016.02); *A61B 90/50* (2016.02); *F16C 11/06* (2013.01); *F16C 11/10* (2013.01); *F16D 63/002* (2013.01); *F16M 13/022* (2013.01); *A61B 34/70* (2016.02); *A61B 2017/00398* (2013.01);

(Continued)

(58) Field of Classification Search
CPC ..... A61B 19/0256; A61B 46/10; A61B 50/20; A61B 50/13; A61B 50/10; A61B 90/50; A61B 46/23; A61B 17/02; A61B 34/70; A61B 2090/508; A61B 2050/105; F16M 13/022; F16C 11/06; F16C 11/10; F16D 63/002; Y10T 403/32311
USPC ........ 403/122, 135, 137, 138, 144; 600/229; 248/288.51; 128/849
See application file for complete search history.

(56) References Cited

U.S. PATENT DOCUMENTS 2,439,973 A * 4/1948 Gunn ....................... D03C 1/06
139/67
3,241,002 A * 3/1966 Smith ................. H02P 29/0016
192/84.1

(Continued)

*Primary Examiner* — Victor MacArthur
(74) *Attorney, Agent, or Firm* — The Law Office of John A. Griecci

(57) ABSTRACT

A multi-joint fixture including a proximal base unit, one or more arms serially connected by electromagnetically lockable ball joints, and a distal hub. The ball joints unlock when not powered. A centering mechanism biases the ball joints toward a neutral position. A control system activates the electromagnetic brake with a high-then-low voltage profile. A headpiece attaches to the hub and holds a drape that covers the fixture. A connector connects a surgical device to the headpiece. A switch on the hub can be actuated via actuators on the headpiece or connector.

8 Claims, 11 Drawing Sheets

Related U.S. Application Data

(60) Provisional application No. 60/810,265, filed on Jun. 1, 2006.

(51) Int. Cl.

| | |
|---|---|
| *F16D 63/00* | (2006.01) |
| *F16M 13/02* | (2006.01) |
| *A61B 46/23* | (2016.01) |
| *A61B 90/50* | (2016.01) |
| *A61B 50/13* | (2016.01) |
| *A61B 50/20* | (2016.01) |
| *A61B 46/10* | (2016.01) |
| *A61B 17/00* | (2006.01) |
| *A61B 50/10* | (2016.01) |
| *A61B 34/00* | (2016.01) |

(52) U.S. Cl.
CPC ........... *A61B 2017/00876* (2013.01); *A61B 2050/105* (2016.02); *A61B 2090/508* (2016.02); *Y10T 403/32311* (2015.01)

(56) References Cited

U.S. PATENT DOCUMENTS

| | | | | |
|---|---|---|---|---|
| 4,796,508 | A * | 1/1989 | Hoshino | F16C 11/106 248/288.51 |
| 4,807,618 | A * | 2/1989 | Auchinleck | A61G 13/12 128/878 |
| 6,371,425 | B2 * | 4/2002 | Fidler | F16M 11/02 248/187.1 |
| 6,398,726 | B1 * | 6/2002 | Ramans | A61B 1/00188 600/112 |
| 2003/0158463 | A1 * | 8/2003 | Julian | A61B 17/00234 600/104 |

* cited by examiner

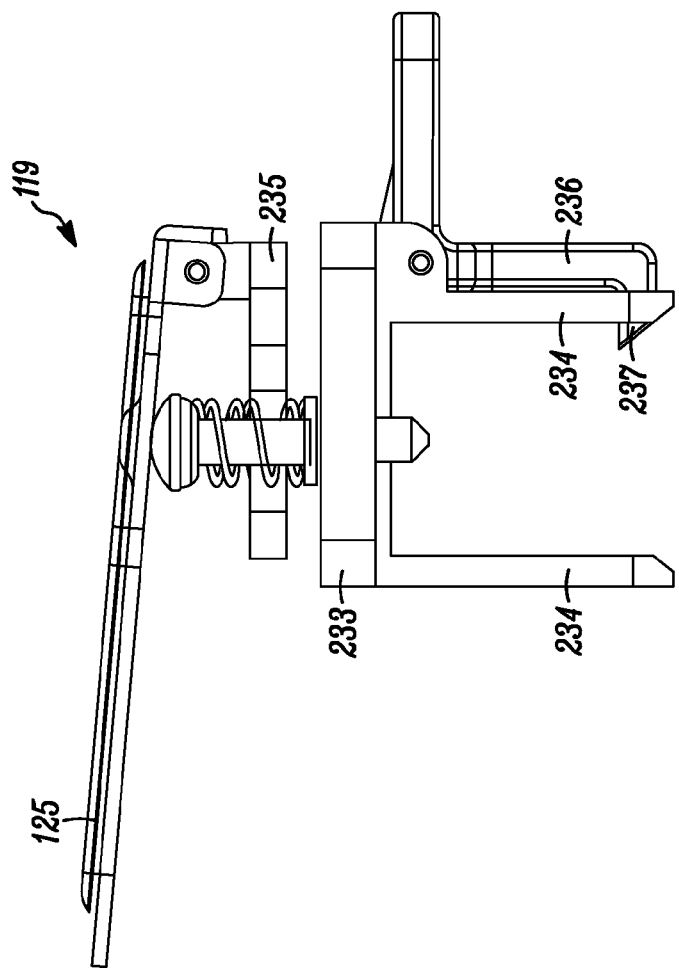
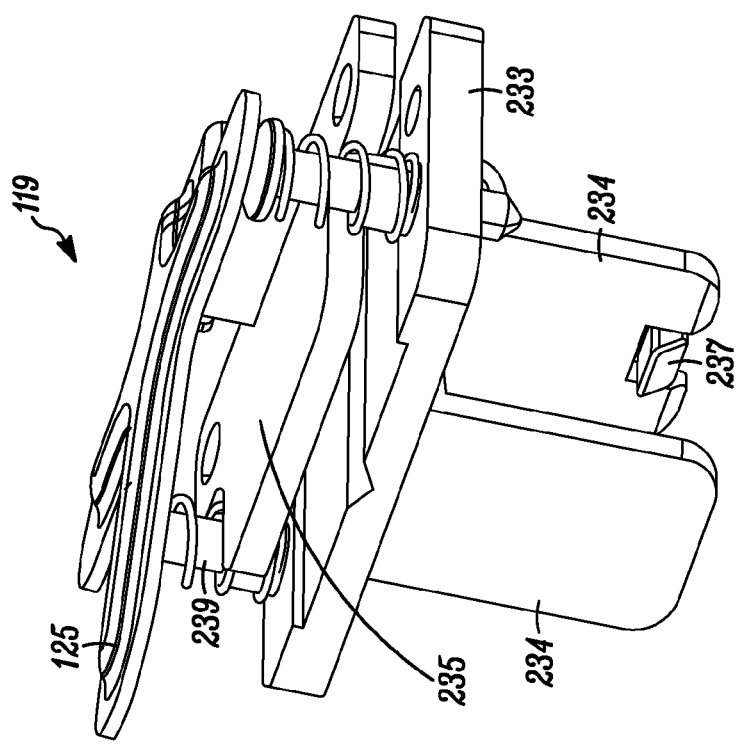
FIG. 7A
FIG. 7B

MULTI-JOINT FIXTURE SYSTEM

This application is a Divisional Application of U.S. patent application Ser. No. 11/809,305, filed May 31, 2007, which claims the benefit of U.S. provisional Application No. 60/810,265, filed Jun. 1, 2006, both of which are incorporated herein by reference for all purposes.

The present invention relates generally to an arm-like fixture for positioning objects such as surgical instruments, and more particularly, to a multi-joint fixture for holding such objects, the fixture having arm segments connected with lockable ball joints.

BACKGROUND OF THE INVENTION

There is a need during various surgical procedures for instruments such as retractors to be held for extended periods of time in stationary positions. Typically, such holding is done by a medical practitioner, such as a surgical assistant, under the direction of a doctor. In some cases, the instruments must be held with some degree of strength, and/or with a great deal of precision. Frequently, the instruments must be held for extended periods of time, causing fatigue in the practitioner holding the instrument, and increasing their risk of the instrument being held with less strength and/or precision than is desirable.

Such instruments are often repositioned several times throughout a surgical procedure. Moreover, such instruments must be placed and held in positions that do not interfere with a doctor's access to various portions of the patient's body. Furthermore, all devices used in a surgical field must either be sterile, or shielded from a patient by a sterile barrier.

Several fixtures for holding retractors and other instruments have been introduced to the industry. Such fixtures tend to be manually intensive and cumbersome, requiring significant labor to position and lock in place. Additionally, many of these fixtures have limited range of motion, often with discrete position settings that can limit their usefulness. Some forms of multi-joint, arm-like support structures are cumbersome and require two-handed operation and/or foot pedal operation, adding complexity to the procedure. While such fixtures might provide consistent holding power, their limited configurations and complex methods of reconfiguring might make their use frequently impractical in the surgical field.

Accordingly, there has existed a need for a medical instrument fixture that is easily and quickly configurable, and provides consistent holding power for instruments. Moreover, the fixture needs to meet the requirements of being usable in a surgical field. Typical embodiments of the present invention satisfy these and other needs, and provide further related advantages.

SUMMARY OF THE INVENTION

In various embodiments, the present invention solves some or all of the needs mentioned above, providing a jointed fixture for holding an object such as a surgical instrument. The fixture includes a base unit, a hub configured to detachably hold the instrument, and a group of one or more arms serially connected by a plurality of joints between the base unit and the hub. The joints are typically ball joints that have a ball, a body containing a portion of the ball, a brake element, and an electromagnetic brake mechanism configured to actuate the brake element between a locked state wherein the brake element, presses against the ball with a force adequate to fix the orientation of the ball, and an unlocked state, wherein the brake element does not press against the ball with a force as high as that of the locked state.

Advantageously, such embodiments provide for a fixture having a high degree of positional flexibility and ease-of-use. More particularly, the plurality of arms and the plurality of ball joints provides for a fixture that can place a surgical instrument in a given position with a variety of different configurations, thereby avoiding configurations that would obstruct a medical practitioner's work. Moreover, the electromagnetic brakes provide for a fixture configuration that is strong, and yet can be locked and unlocked rapidly with the press of a single button.

The invention may further provide for lever arms that leverage the force of the electromagnetic actuators to increased levels of force. Such lever arms advantageously allow the use of electromagnets that consume less power and are smaller, lighter in weight and less expensive.

The invention may further provide the fixture with ball joint centering mechanisms that bias ball joint positions toward a single, neutral (center) position. Such centering mechanisms typically provide the fixture with a single, predictable configuration (or limited number of configurations) having a minimum potential energy for most any position of the surgical instrument. Moreover, the invention may further provide for a level of joint rigidity while the joints are unlocked.

Thus, for any surgical-instrument position, the fixture will have a natural and predictable, low-energy configuration toward which it tends to move, and a medical practitioner can adjust to other configurations as desired prior to locking the ball joints. Moreover, the joint rigidity of the fixture will tend to resist movement even when unlocked, thereby providing the fixture a supple yet damped movement that is not limp or susceptible to significant oscillation.

A surgical drape may be used to cover the fixture to maintain the sterility of a surgical field, the drape having a headpiece that is intermediate the distal end of the fixture and the surgical instrument. A switch to control the electromagnetic locks may be provided at the distal end of the fixture and within the drape. An actuator may be placed on or adjoining the surgical instrument and external to the drape, the actuator being configured to actuate the switch through a hermetically sealed portion of the headpiece. A medical practitioner may therefore control the position of the surgical instrument and control the electromagnetic brakes with a single hand external to the drape, leaving the other hand free, and not exposing the surgical field to possible contaminants on the fixture.

A control system of the invention is configured to actuate the electromagnetic brake mechanisms with a voltage profile characterized by a first, transient portion and a second, steady-state portion that is less than the transient portion in voltage level. Advantageously, the voltage profile provides for the electromagnets to initially assure that they fully actuate to apply maximum locking forces on the ball joints, and do so without needing to use electromagnets large enough to maintain such power levels for extended periods, and without using the power required to maintain such high power levels throughout a surgical procedure.

Other features and advantages of the invention will become apparent from the following detailed description of the described embodiments, taken with the accompanying drawings, which illustrate, by way of example, the principles of the invention. The detailed description of particular described embodiments, as set out below to enable one to build and use an embodiment of the invention, are not intended to limit the enumerated claims, but rather, they are intended to serve as particular examples of the claimed invention.

BRIEF DESCRIPTION OF THE DRAWINGS

FIG. 7A is a perspective view of a surgical-instrument adapter as used in the multi-joint fixture depicted in FIG. 1.

FIG. 7B is a left side view of the surgical-instrument adapter depicted in FIG. 7A.

DETAILED DESCRIPTION OF THE EMBODIMENTS

The invention summarized above and defined by the enumerated claims may be better understood by referring to the following detailed description, which should be read with the accompanying drawings. This detailed description of particular described embodiments of the invention, set out below to enable one to build and use particular implementations of the invention, is not intended to limit the enumerated claims, but rather, it is intended to provide particular examples of them.

Typical embodiments of the present invention reside in a jointed fixture system for use in surgical procedures with an operating table, the various components of the system, and methods of using the same.

Figure 1:
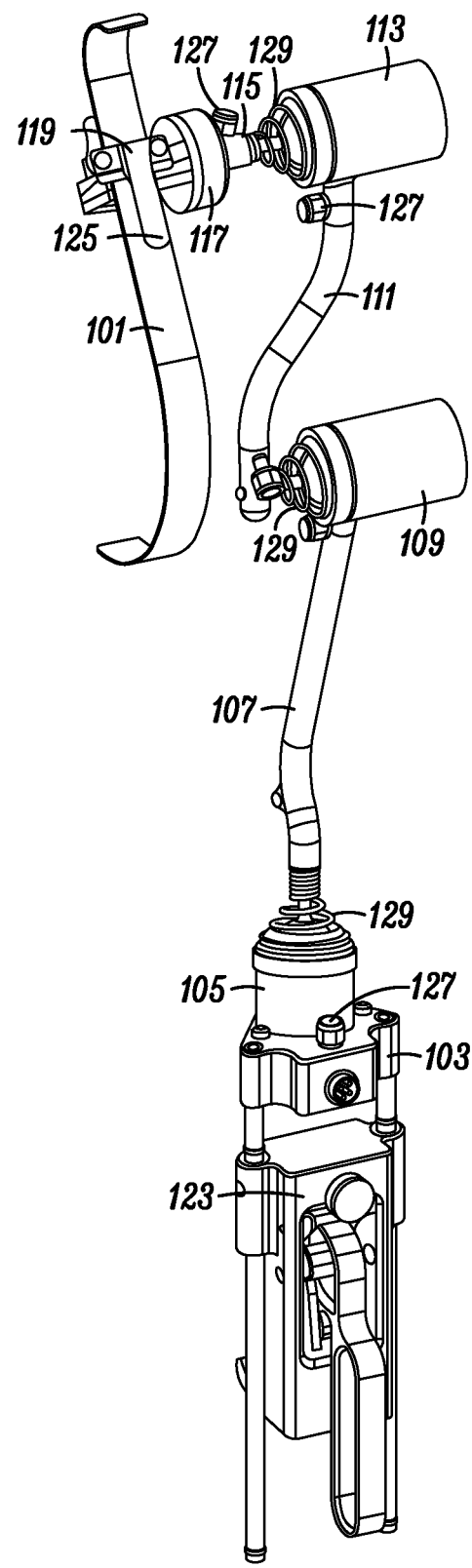
FIG. 1 is a perspective view of a surgical retractor attached to a multi-joint fixture that includes a headpiece of a surgical drape, with a sterile curtain of the surgical drape and three tethers not being depicted.

With reference to FIG. 1, a first embodiment of the invention forms a multi-joint fixture for holding a surgical instrument 101 such as a surgical retractor (shown), an endoscope, a limb positioner, or the like. In this context, the term instrument should be understood to include any useful object that a medical practitioner might wish to be held stationary during surgery.

The fixture includes a base unit 103, a first joint 105, a first arm 107, a second joint 109, a second arm 111, a third joint 113 and a fixture hub 115. The first joint adjustably connects a proximal end of the first arm to the base unit, the second joint adjustably connects a proximal end of the second arm to a distal end of the first arm, and the third joint adjustably connects the fixture hub to a distal end of the second arm. The fixture thus includes a plurality of three joints interconnecting a plurality of four members (including the two arms), each joint having an attached member to which it is rigidly attached and a connected member that it can allow to rotate with respect to the attached member.

Typically, the first joint is rigidly attached to the base unit and is connected to the first arm, the second joint is rigidly attached to the first arm and is connected to the second arm, and the third joint is rigidly attached to the second arm and is connected to the fixture hub. This series of connections prevents each joint from having to carry its own weight, potentially making the multi-joint fixture a more reliable and stable device.

Each ball joint defines a longitudinal axis, along which its elements are positioned. The longitudinal axis also forms a neutral position for the ball joint, which will be referred to as a center position. The first ball joint 105 is configured with its longitudinal axis aligned with (and passing through the center of) its attached member (the base 103) and aligned with the general direction of its connecting member (the first arm 107). The second ball joint 109 is configured with its longitudinal axis perpendicular to the general directions of both its attached member (first arm 107) and its connected member (second arm 111). The third ball joint 113 is configured with its longitudinal axis perpendicular to the general direction of its attached member (second arm 111), but aligned with its connecting member (the fixture hub 115).

Figure 2:
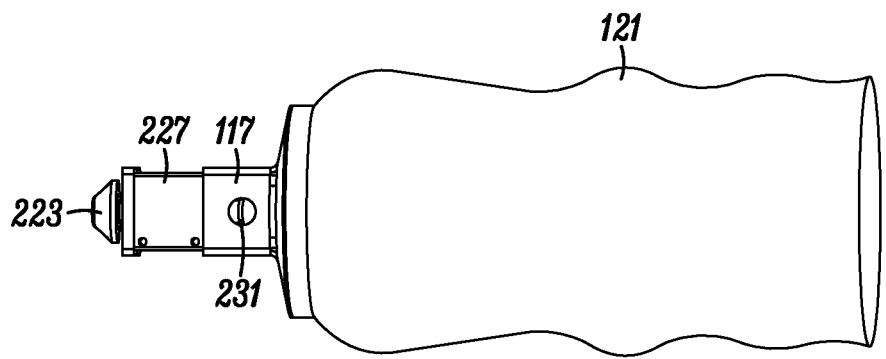
FIG. 2 is a perspective view of the surgical drape of FIG. 1, including a shortened view of the sterile curtain that was not depicted in FIG. 1.

With reference to FIGS. 1 & 2, the fixture hub 115 is configured to detachably receive and connect to a headpiece 117 of a sterile surgical drape. The headpiece is configured with a drape hub to detachably receive and connect to (and thereby hold) a surgical-instrument adaptor 119 that is attached to the surgical instrument 101.

The surgical drape includes a sterile curtain 121 (not depicted in FIG. 1) that is generally tubular in shape (tapering slightly from a smaller diameter at a distal end near the headpiece to a larger diameter at a proximal end) and at least as long as the entire multi-joint fixture. The headpiece 117 is internally configured to form a sterile barrier. At the distal end, the sterile curtain is hermetically sealed around a periphery of the headpiece. Thus, with the headpiece connected to the fixture hub 115, the surgical drape can be extended over the multi-joint fixture before a surgical procedure, thereby maintaining a sterile environment in the surgical field without having to sterilize the multi-joint fixture itself. The sterile drape will typically be a single-use, disposable device that is provided in a sterile state within hermetically sealed packaging.

The base unit 103 is typically mounted to a rail clamp 123, which is configured with a mechanism to clamp onto a rail of an operating table. The clamping mechanism can be a screw clamp as is commonly used, or a quick connect mechanism, as is depicted. Alternatively, the base unit may be otherwise positioned with respect to the operating table, for example, being attached to a floor stand or permanently affixed (i.e., not readily removable from) the operating table or some nearby device.

The plurality of ball joints (i.e., the first, second, and third ball joints) are each configured with an electromagnetic brake that can be actuated between a locked and an unlocked state. In the locked state each ball joint is locked from any rotational movement, thereby firmly holding the members that the joint connects in a substantially rigid relationship. Thus, in their locked states, the first ball joint 105 holds the base unit 103 and the first arm 107 in a substantially rigid relationship, the second ball joint 109 holds the first arm 107 and the second arm 111 in a substantially rigid relationship, and the third ball joint 113 holds the second arm 111 and the fixture hub 115 in a substantially rigid relationship. In this context, the term substantially rigid should be understood to indicate that it is rigid enough to hold surgical instruments, such as retractors, with adequate force for use in surgery.

In the unlocked state, each ball joint is free to allow movement between the members that the joint connects without the application of undue force. Thus, in their unlocked states, the plurality of ball joints provide for the surgical instrument 101 to be positioned in a wide variety of positions (i.e., locations and orientations). Additionally, for most surgical-instrument positions, the arms and ball joints can be placed in a variety of configurations so as to avoid obstructing the work of medical practitioners. Moreover, while this system has an arm-like configuration wherein the first, second and third joints effectively operate as shoulder, elbow and wrist joints, respectively, it has even greater flexibility of configuration than a human arm, in that it uses three ball joints.

The surgical-instrument adaptor 119 includes a surgical-instrument switch actuator 125 that can be actuated by a medical practitioner between a free position and an actuated position. This surgical-instrument switch actuator is biased by a spring toward the free position. The surgical-instrument switch actuator is part of a switch system configured such that, when the surgical-instrument switch actuator is in the free position, the electromagnetic brake of each ball joint is actuated to the locked state, and when the surgical-instrument switch actuator is in the actuated position the electromagnetic brake of each ball joint is actuated to the unlocked state. Optionally, the switch system may be adapted as a multiple position switch system, or as a system including a plurality of switches, to separately control the actuation of the electromagnetic brakes of the ball joints so that various combinations of the electromagnetic brakes can be actuated without actuating the remaining brake(s).

While it is advantageous for medical practitioners to have flexibility of fixture configuration for desired surgical-instrument positions, it is also advantageous for movements of the fixture to be predictable and supple, but not limp. To this end, each ball joint is configured with a centering mechanism 129 that provides a spring-based or spring-like restoring force that biases (i.e., actuating or driving) the ball of the ball joint to a neutral (center) position (i.e., location and/or orientation). As a result, for every surgical-instrument position there will typically be a fixture configuration having the lowest combined potential energies of the three centering mechanisms, and the fixture will tend toward moving to that fixture configuration unless stopped by some other force (such as optional manipulation by a medical practitioner). Center, in this context, should be understood as referring to the central position of the spring bias.

While in the unlocked state, each ball joint may maintain some joint rigidity (i.e., resistance to movement) between the members that the joint connects. The typical level of resistance is set at a level high enough to damp the motion of the fixture and avoid sloppiness and oscillation, and low enough to provide for a medical practitioner to easily manipulate the location of the surgical instrument and the configuration of the fixture. It is noteworthy that the joint rigidity will frequently work against the restoring force of the centering mechanism 129. The combination of the joint rigidity with the restoring force provides for a fixture that can be positioned and used with a minimum of attention and effort.

Figure 3:
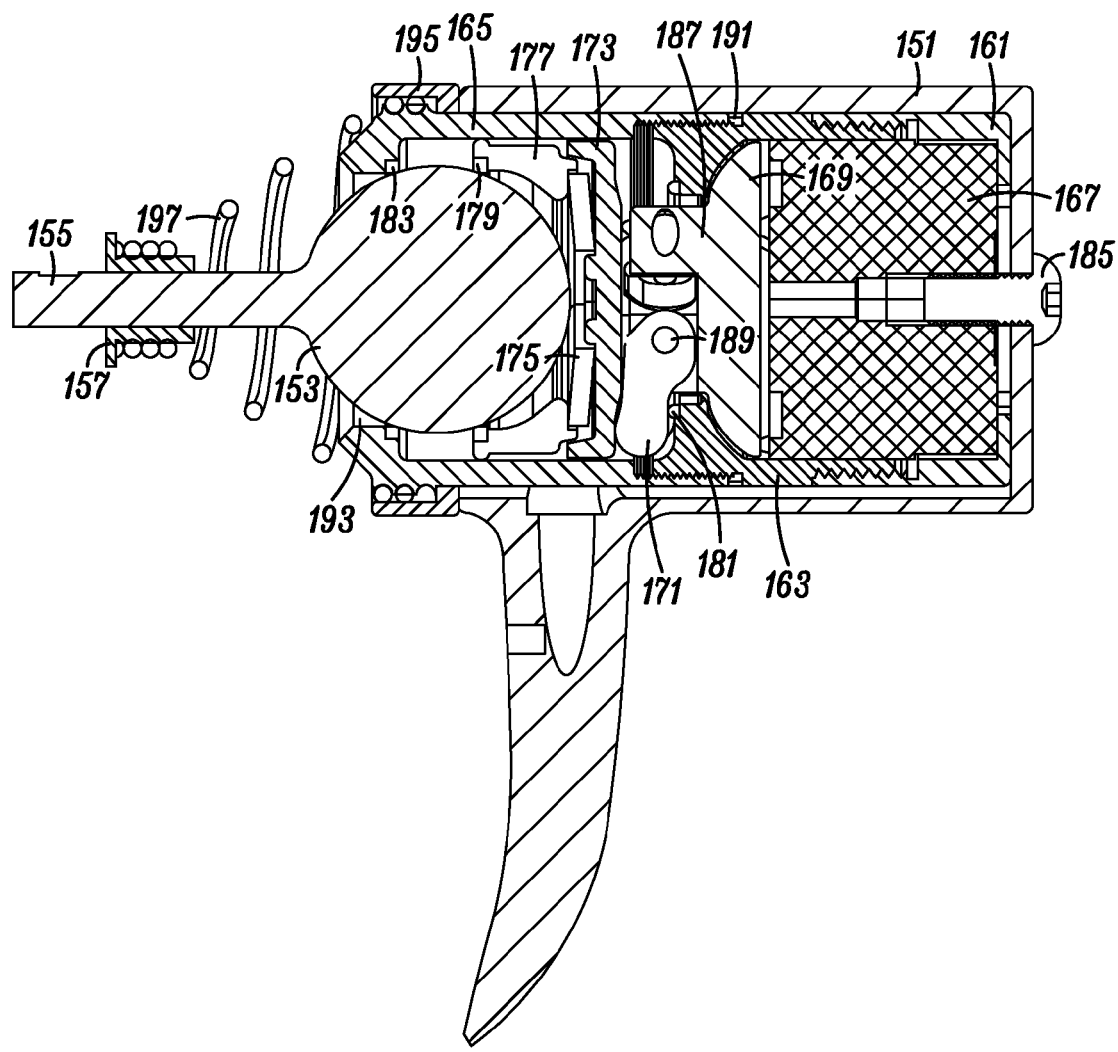
FIG. 3 is a front cross-section view of a ball joint as used in the multi-joint fixture depicted in FIG. 1.
Figure 4A:
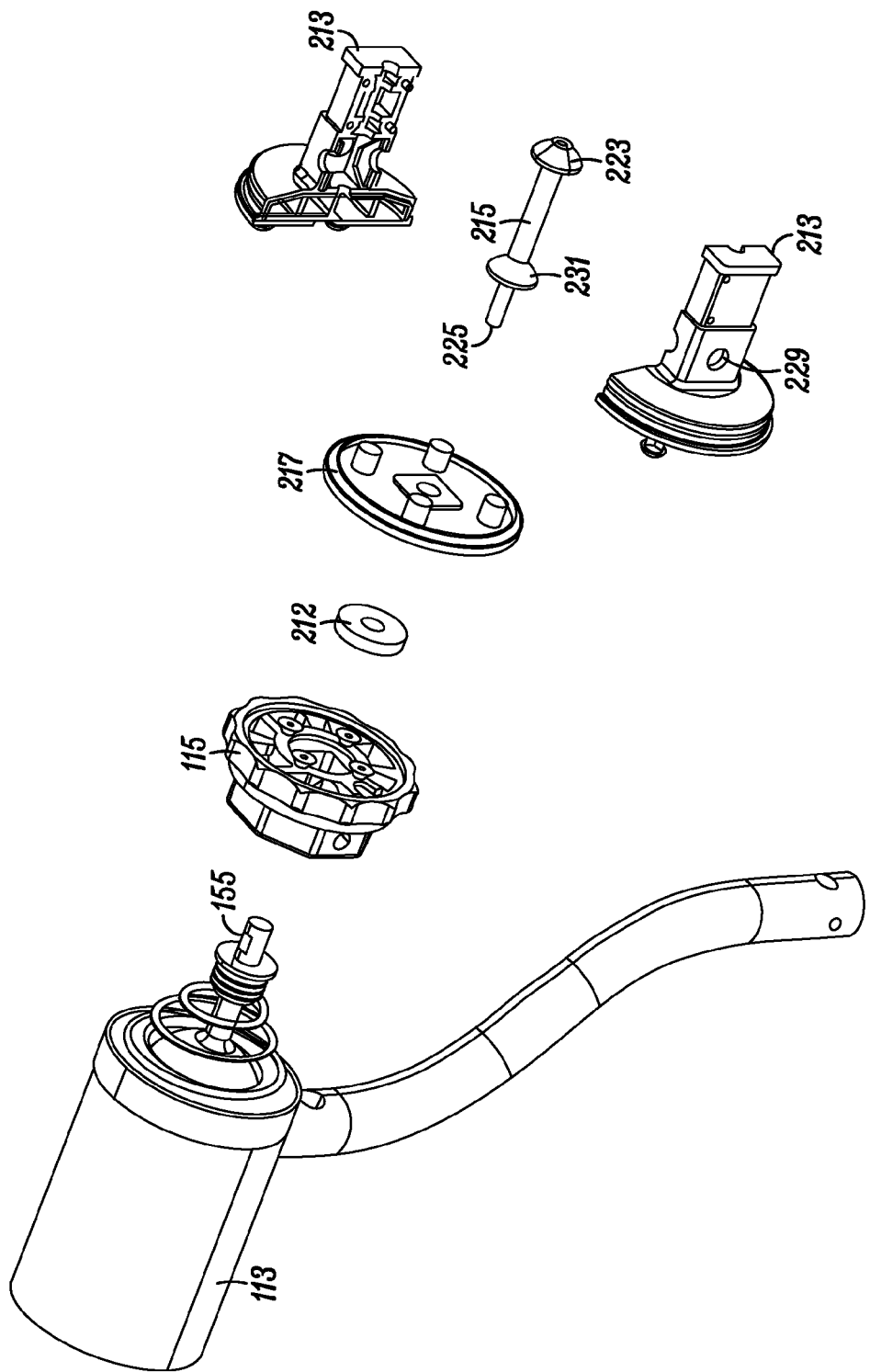
FIG. 4A is an exploded rear perspective view of a third ball joint, a fixture hub, and the headpiece of the multi-joint fixture, as depicted in FIG. 1.
Figure 4B:
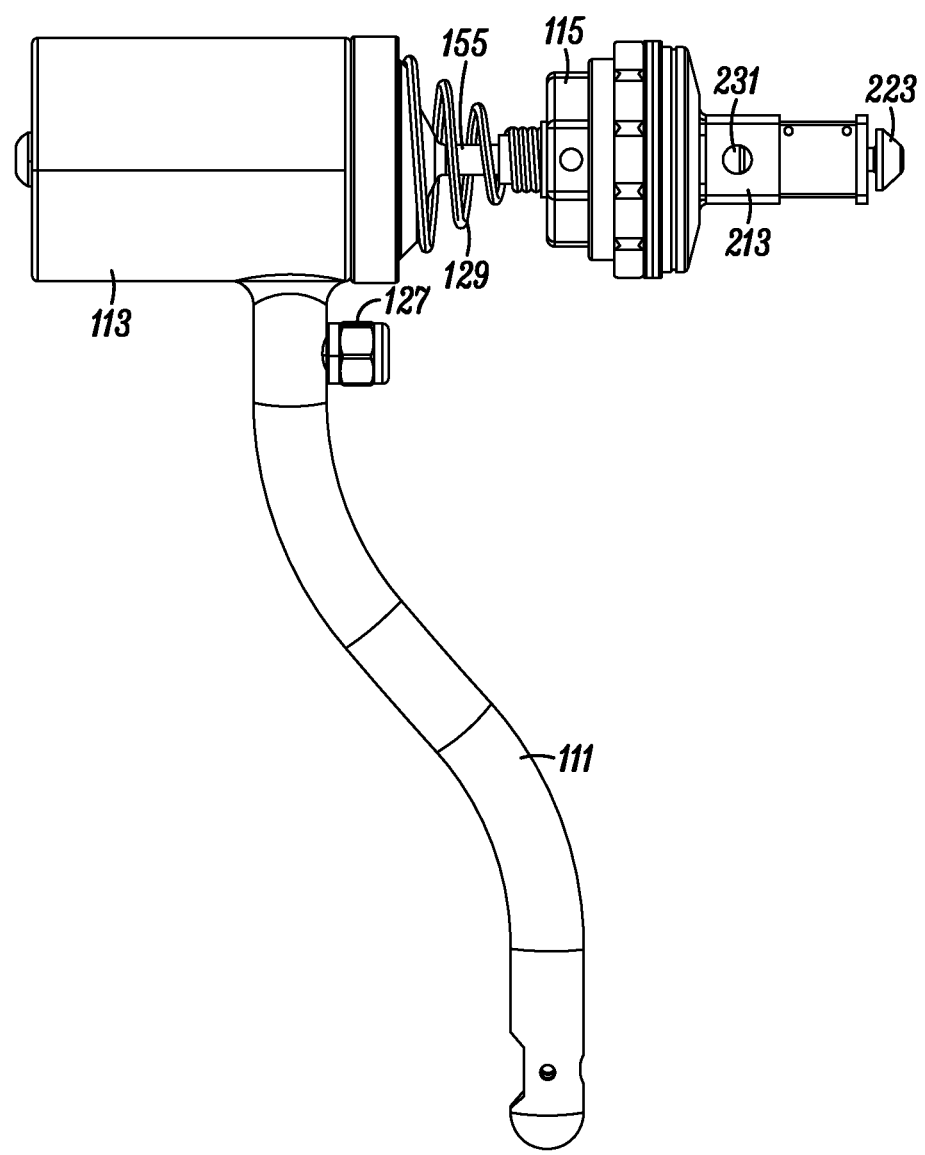
FIG. 4B is a rear view of the third ball joint, the fixture hub, and the headpiece depicted in FIG. 4A.
Figure 6:
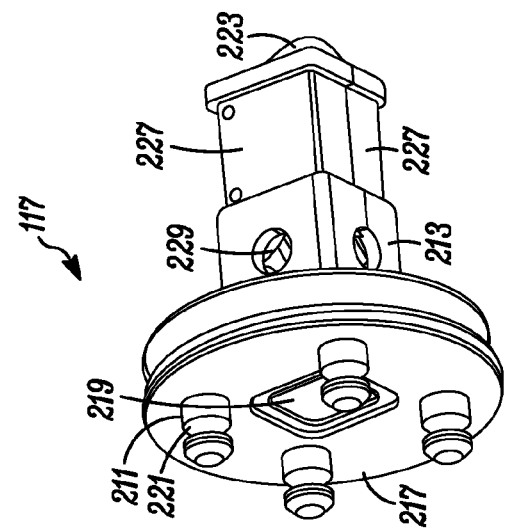
FIG. 6 is a perspective view of the headpiece depicted in FIG. 4A.
Figure 5B:
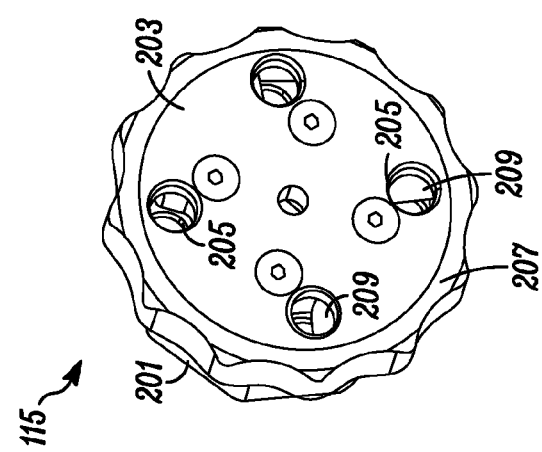
FIG. 5B is a second perspective view of the fixture hub depicted in FIG. 4A.
Figure 5A:
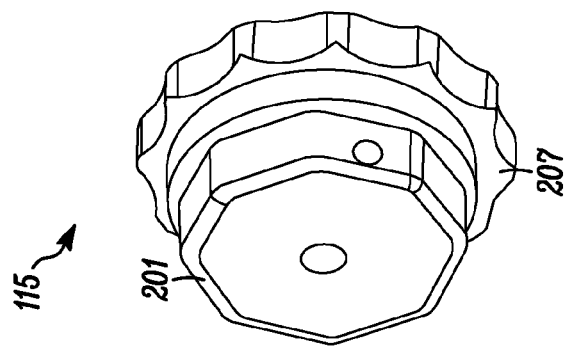
FIG. 5A is a perspective view of the fixture hub depicted in FIG. 4A.
Figure 8:
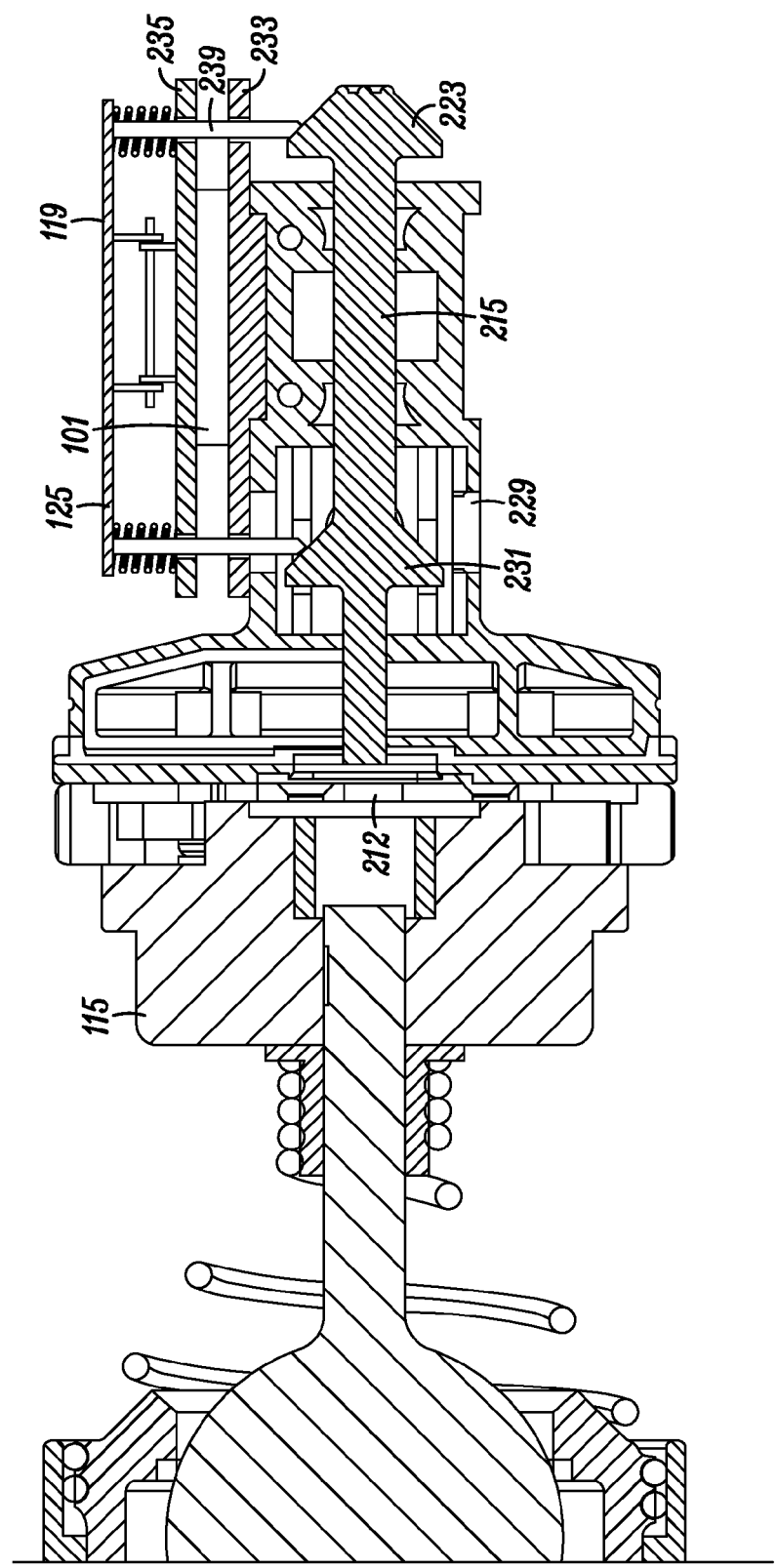
FIG. 8 is a rear cross-sectional view of the third ball joint, the fixture hub, and the headpiece depicted in FIG. 4A, with the surgical-instrument adapter of FIG. 7 connected to the headpiece.

With reference to FIGS. 1 & 3, each of the ball joints includes an outer housing 151, a ball, the ball-centering mechanism, and the electromagnetic brake mechanism. The outer housing is affixed to or unitary with the rigidly attached member. The ball includes a spherical portion 153 and a shaft 155. The shaft extends from a proximal end affixed to the spherical portion to a distal end, the distal end serving as an attachment point for the connected member.

The joint of this embodiment is modular, having an inner housing that is removably received within the outer housing 151 along the longitudinal axis. The inner housing includes a first housing portion 161, a second housing portion 163 and a third housing portion 165 serially connected with threaded connections. The electromagnetic brake is comprised of the inner housing, an electromagnet 167, a draw-plate 169, a plurality of three lever arms 171, a keel 173, a spring element in the form of a Belleville washer 175, a thrust-cup 177, and a first hardened ring 179 (the brake ring). The second housing portion 163 is provided with a hardened reaction ring 181, and the third housing portion 165 is provided with a second hardened ring 183 (the retaining ring). Each hardened ring is characterized by a central axis that is concentric with and parallel to the longitudinal axis of the ball joint.

A screw 185 is inserted along the longitudinal axis, through the outer housing 151 and the inner housing first housing portion 161, to be threadedly received in the electromagnet 167, thereby holding the electromagnet and the first housing portion rigidly with respect to the outer housing portion. The second housing portion 163 is threadedly received along the longitudinal axis on the first housing portion, and contains the draw-plate 169, which is held apart from the electromagnet (as described below) along the longitudinal axis at a distance creating a small air gap (between the electromagnet and the draw-plate) normal to the longitudinal axis (i.e., the gap generally establishes a plane to which the longitudinal axis is perpendicular).

The draw-plate 169 includes three posts 187 defining holes for three pins 189 that connect the draw-plate to the three lever arms 171, but allow each lever arm to rotate around its respective pin. The lever arms extend radially outward from the draw-plate posts, circumferentially spaced at 120° angles, over the reaction ring 181, such that an outer end of each lever arm contacts the keel 173 at locations radially outside of the reaction ring.

The third housing portion 165 is threadedly received along the longitudinal axis on the second housing portion 163. Using a shim 191, the longitudinal spacing of the second and third housing portions is set such that the keel 173 presses down against the outer ends of the lever arms 171, making the lever arms act as levers, with the reaction ring 181 acting as their fulcrums, to pull the draw-plate 169 away from the electromagnet 167 and establish the gap (i.e., the air gap between the draw-plate and the electromagnet, through which the draw-plate can be actuated by the electromagnet).

The third housing portion 165 contains a substantial part of the ball, and the shaft 155 extends out from an orifice 193 of the third housing portion. The first and second hardened rings 179 & 183 have diameters smaller than the diameter of the spherical portion 153 of the ball. They are concentrically located along the ball joint longitudinal axis on longitudinally opposite sides of the center of the spherical portion, and are in contact with the spherical portion. The second hardened ring 183 is a retaining ring in that it retains the spherical portion of the ball within the housing, thus making the joint a non-separable joint (i.e., the ball cannot separate from the assembled joint). The thrust cup 177 is configured to drive the first hardened ring along the longitudinal axis toward the second hardened ring such that these two rings hold the spherical portion in place and frictionally resist its rotational movement.

When the second and third housing portions 163 & 165 are threadedly attached and properly shimmed, the Belleville washer 175 is compressed between the thrust cup 177 and the keel 173, defining relaxed-state reaction forces between the thrust cup and the keel. The relaxed-state reaction force on the thrust cup drives the first hardened ring towards the second hardened ring and against the spherical portion of the ball. The longitudinal length of the shim 191 and a spring constant of the Belleville washer 175 are configured such that the relaxed state reaction force on the thrust cup drives the first hardened ring towards the second hardened ring with the proper amount of force to establish the joint rigidity of the ball joint, and thus the presence of the relaxed-state reaction force establishes the unlocked state of the ball joint.

The relaxed-state reaction force on the lever arm by the keel is reacted over the reaction ring 181, pulling the draw-plate 169 away from the electromagnet 167, to maintain the gap. The configuration of the reaction ring and the lever arms provides a four to one leverage ratio for each lever arm. Thus, the longitudinal force between the keel and each lever arm is four times the longitudinal force between each lever arm and the draw-plate. When the electromagnet is not energized, there are no system forces drawing the draw-plate toward the electromagnet against the pull of the lever arms.

The electromagnet 167 is not energized when the surgical-instrument switch actuator 125 is actuated to the actuated position. When the surgical-instrument switch actuator is released, a spring bias actuates the surgical-instrument switch actuator to the free position, which causes the electromagnet to be energized. The energized electromagnet draws the draw-plate 169 down toward the electromagnet to close the gap. The draw-plate in turn pulls an inner end of each lever arm 171 down over its portion of the reaction ring 181 which acts as a fulcrum for the lever arm to push up on the keel 173. Because of the four to one leverage of each lever arm, the keel is pushed with four times as much force as the draw-plate is pulled down by the electromagnet.

The upward movement of the keel 173 further compresses the Belleville washer 175, defining energized-state reaction forces between the thrust cup and the keel. The energized-state reaction force on the thrust cup presses the first hardened ring 179 against the spherical portion of the ball and towards the second hardened ring 183 to statically hold the spherical portion of the ball and lock the ball joint from any rotational movement, thereby firmly holding the members that the joint connects in a substantially rigid relationship. The presence of the energized-state reaction force establishes the locked state of the ball joint.

Thus, each ball joint has an electromagnetic brake mechanism configured to switch between locked and unlocked states, wherein the orientation of the ball within the body is statically held when the brake mechanism is in the locked state, and wherein the application or removal of electrical energy switches the brake mechanism between the locked and unlocked states. Relative to the unlocked state, in the locked state the keel is actuated toward the ball and the thrust cup and first hardened ring press against the ball with greater force.

Each ball joint 105, 109 & 113 is further configured with a neutral-bias centering mechanism 129 in the form of a retaining cap 195 and a spring 197 spiraling in three dimensions (such as in the shape of a conical spring). The spring is concentric with the longitudinal axis, and extends longitudinally from a wide-radius end to a small-radius end. The wide-radius end is received in helical grooves around an exterior of the third housing portion 165, longitudinally closer to the center of the spherical portion 153 of the ball. The small-radius end is wound around, and thereby connected to, a bushing 157 located distantly along the shaft 155. The retaining cap surrounds the wide-radius end of the spring and retains it in place.

This spring 197 is configured to laterally react against the shaft 155 so as to drive it laterally back toward the neutral position on the longitudinal axis when it is not already there. Optionally, this spring may also be configured to react against the shaft in axial rotation so as to rotate it back to a neutral position orientation. Additionally, the spring may be preloaded such that it axially pulls the shaft away from the third housing portion, thus preloading the spherical portion of the ball against the second hardened ring, and thereby contributing to the joint rigidity of the ball joint.

The ball joint of this first embodiment is of a linear configuration in that its actuation and braking elements (e.g., an electromagnet, a draw-plate that establishes a closable gap with the electromagnet, and a plurality of brake elements) extend along a single longitudinal axis, along which its electromagnet gap is closed and its primary brake elements (the first and second hardened rings) and secondary brake elements (the third housing portion and the thrust cup) react. It is also of a levered configuration that leverages the electromagnet force, in that the three lever arms provide a four to one mechanical advantage, allowing for a smaller electromagnet to be used to produce a given level of force.

With reference to FIGS. 1, 2, 4A, 4B, 5A & 5B, the fixture hub 115 is longitudinally received on the shaft 155 of the third joint ball (i.e., longitudinally along the ball joint axis). The fixture hub includes a body 201 that is pinned or otherwise affixed to the shaft. A cover plate 203 (not shown in FIG. 4A) is attached to the body on a distal side of the body, and defines four slots 205 for receiving four pins 211 of the headpiece 117. A lock ring 207 is held intermediate the cover plate and the body. The lock ring can rotate between an open position and a locked position, and is spring biased toward the locked position. The lock ring has four tabs 209 that extend partially across the four slots of the cover plate when the lock ring is in the locked position, but not when it is in the open position, thus configuring the fixture hub to removably receive the headpiece.

The fixture hub 115 includes an electrical switch 212 facing distally on its distal side. This electrical switch, which is a part of the switch system, forms an electrically closed circuit when in a not-pressed state, and an electrically open circuit when in a pressed state. The electrical switch is directly wired to a tether connector 127 (not shown in FIGS. 4A, 4B, 5A & 5B) of the fixture hub, and is in control of the electromagnetic brakes of each joint (as is described later). When the fixture hub does not have a headpiece 117 attached thereon, the electrical switch may be manually actuated by a medical practitioner to unlock the electromagnetic brakes of the three joints when pressed (to form an open circuit), and to lock the electromagnetic brakes of the three joints when released (to form a closed circuit).

The headpiece 117 includes a body 213, a headpiece switch actuator 215, a base plate 217, a flexible button pad 219, and the four pins 211 that are received by the fixture hub. The pins extend proximally from a proximal face of the headpiece. The pins include grooves 221 in which the tabs 209 of the lock ring 207 can be received to lock the headpiece onto the fixture hub 115 when the proximal face of the headpiece is received against the cover plate 203 on the distal side of the fixture hub.

The headpiece body 213, which may be formed in two halves and assembled, contains the headpiece switch actuator 215, which is a part of the switch system. The headpiece switch actuator extends longitudinally through the headpiece body, from a distal knob 223 to a proximal tip 225. The distal knob extends distally beyond a distal end of the headpiece body. The proximal tip extends through an orifice in the center of the base plate 217 and presses against the button pad 219, which extends across a proximal face of the base plate (which in turn forms the proximal face of the headpiece). The headpiece switch actuator is longitudinally slidable from a distal position to a proximal position, and may be spring loaded toward the distal position.

With the headpiece 117 attached to the fixture hub 115, the proximal tip 225 of the headpiece switch actuator 215 is in close proximity to the electrical switch 212 of the fixture hub 115, with the button pad 219 extending therebetween. With the headpiece switch actuator 215 in its distal position, the electrical switch is in its not-pressed state. When the headpiece switch actuator is slid from its distal position to its proximal position, the proximal tip of the headpiece switch actuator flexibly extends the button pad and presses the electrical switch, causing the electrical switch to form an open circuit.

Because the distal knob 223 extends distally from the distal end of the headpiece body, a medical practitioner may manually actuate the electrical switch by pressing on the distal knob. Thus, the medical practitioner can still actuate and release the electrical switch when the surgical drape is received on the multi-joint fixture over the electrical switch (i.e., when the headpiece 117 is connected to the fixture hub 115 and the sterile curtain 121 is extended over the multi-joint fixture).

The button pad 219 is hermetically sealed to the base plate 217, and the sterile curtain 121 is hermetically sealed around the periphery of the base plate. Thus, the surgical drape effectively forms a complete sterile barrier between a patient in the surgical field and the multi-joint fixture.

With reference to FIGS. 2, 4A, 4B & 6, the headpiece body 213 defines a headpiece hub in the form of a protrusion having a generally square cross-section, a distal end of which forms the distal face of the headpiece body from which the distal knob 223 protrudes. The hub protrusion forms a groove 227 around its perimeter, and four access holes 229, one access hole being on each side of the square perimeter. The four access holes provide external access from all four sides of the protrusion to an intermediate knob 231 on the headpiece switch actuator 215 intermediate its distal knob 223 and its proximal tip 225.

Both the distal knob 223 and the intermediate knob 231 form conical surfaces concentric with the longitudinally extending headpiece switch actuator 215. The conical surfaces extend from a wide radius at a proximal end of each knob to a narrow radius at a distal end of the knob. As a result, a lateral force against the conical face of either knob will tend to drive the headpiece switch actuator toward its proximal position.

With reference to FIGS. 1, 7A, 7B & 8, the surgical-instrument adapter 119 includes a connector 233, a lockdown 235, and the surgical-instrument switch actuator 125. The lockdown 235 is configured to rigidly clamp the surgical instrument 101 onto, and affix (connect) it to, the connector 233. In use, it is anticipated that a different surgical-instrument adapter will be permanently affixed to each surgical instrument to be used with the multi-joint fixture. Thus, each surgical-instrument adapter is constructed to withstand repeated sterilization and use with its surgical instrument. Optionally, the surgical-instrument adapter and the surgical instrument may be integral, offering cost, weight and size advantages in the construction and use of the resulting surgical instruments with integral adapters.

The surgical-instrument adapter connector 233 is configured with flanges 234 sized and spaced to be conformingly received over the groove 227 of the headpiece hub. The connector 233 and headpiece hub are mutually configured such that the connector can be placed onto any of the four sides of the hub, and oriented in either of the two lateral directions for that hub-side, thereby forming a total of eight different connection configurations. The connector 233 is further configured with a spring-loaded connector lock mechanism 236 having a tab 237 positioned for gripping the headpiece hub when the connector is received on the hub, thus making the connector quickly detachable from the hub.

The surgical-instrument switch actuator 125 is hingedly attached along a hinge axis to the connector 233 and lockdown 235. The surgical-instrument switch actuator includes two pins 239, each extending down through a separate orifice that extends through the connector 233 and lockdown 235. The pins are offset from the hinge axis such that each pin is driven down through its respective orifice when the surgical-instrument switch actuator is actuated from its free position to the actuated position, such as by a finger of a medical practitioner. The surgical-instrument switch actuator further includes two springs configured to drive the surgical-instrument switch actuator and each pin back up when the medical practitioner's finger releases the surgical-instrument switch actuator, allowing it to return to its free position.

The pins 239 are positioned and oriented on the connector 233 such that, with the connector received on the headpiece hub, each pin aligns with and extends to the conical surface of one knob of the headpiece switch actuator 215. The four access holes 229 are configured to provide the pins access to the intermediate knob 231 from any of the four sides of the hub. No access holes are required to reach the distal knob 223, as it extends distally outward from the distal end of the headpiece body.

Accordingly, for a given configuration of the surgical-instrument adapter 119 mounted on the headpiece hub, a first pin will press against the distal knob 223, and a second pin will press against the intermediate knob 231. Thus, when the surgical-instrument switch actuator is pressed, the pins drive the conical surfaces of both knobs of the headpiece switch actuator to press the electronic switch. It may be noted that when the surgical-instrument adapter 119 is repositioned on the headpiece hub such that it is on the same side of the hub, but extending in the opposite lateral direction, the pin positions will be reversed and the first pin will press against the intermediate knob 231, while the second pin presses against the distal knob 223.

The surgical-instrument adapter 119 is adapted to be connected to the surgical instrument 101 in a position where the surgical-instrument switch actuator 125 can be conveniently actuated by a medical practitioner's hand that is holding the surgical instrument. Using just one hand a medical practitioner may both hold the surgical instrument and manually actuate the electrical switch 212 by pressing on the surgical-instrument switch actuator 125. Thus, with one hand the medical practitioner can hold the surgical instrument and actuate or release the electromagnetic brakes while the surgical drape is received on the multi-joint fixture and the surgical instrument is attached to the headpiece of the surgical drape.

As described above, this switch system, which controls the electromagnetic brake of each joint, includes the electrical switch 212 on the fixture hub 115, the headpiece switch actuator 215 on the headpiece of the surgical drape, and the surgical-instrument switch actuator 125 on the surgical-instrument adapter 119, which is connected to the surgical instrument 101. The electrical switch 212 may be directly accessed when the surgical drape is not connected to the fixture hub. The electrical switch may be indirectly accessed by pressing on the headpiece switch actuator when the surgical drape is connected to the fixture hub, but no surgical instrument is connected to the headpiece of the surgical drape. And finally, the electrical switch may be indirectly accessed by pressing on the surgical-instrument switch actuator 125 when the surgical drape is connected to the fixture hub and a surgical instrument is connected to the headpiece of the surgical drape.

In an alternative variation, the headpiece body may be unitary, and may extend longitudinally past the distal knob. In this variation, the body will define an additional four access holes for the surgical-instrument adapter pin that is to contact the distal knob. Also, the switch actuator has a distal extension extending past the distal knob, providing manual access to the headpiece switch actuator when the surgical drape is connected to the fixture hub, but no surgical instrument is connected to the headpiece of the surgical drape.

Figure 9:
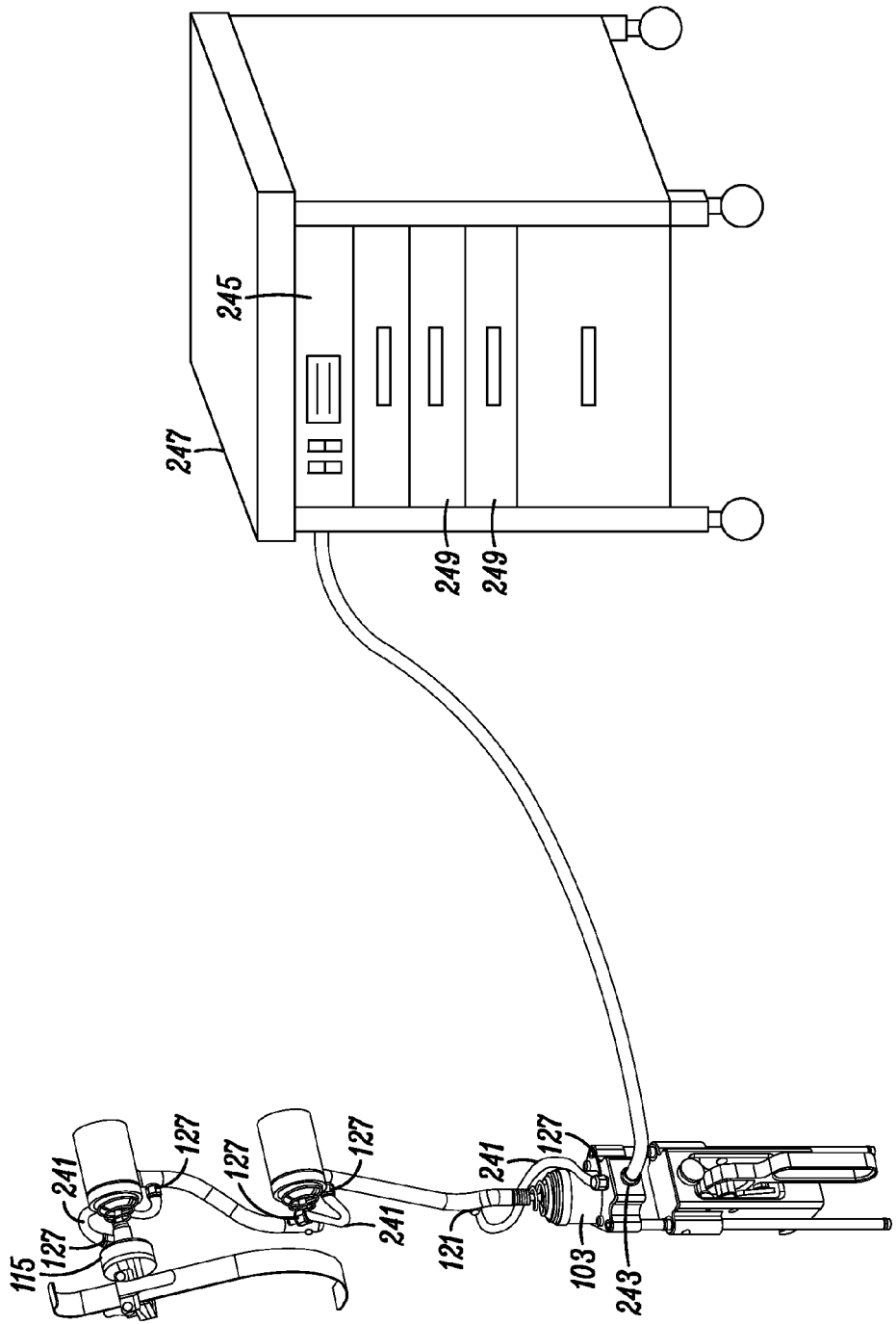
FIG. 9 is a system diagram of a multi-joint fixture system, including the retractor and multi-joint fixture depicted in FIG. 1.

With reference to FIGS. 1 & 9, to facilitate communication between the switch system and each electromagnetic brake, each arm forms a hollow tube in which electrical wiring extends. At either end of each arm wiring exits the hollow tube via a tether connector 127. Tether connectors are also located on the base unit 103 and the fixture hub 115 (as noted above). External, hollow tethers 241 extend between tether connectors on either side of each joint. Each tether provides a passageway for the wiring to extend between externally around a given joint, between the tether connectors on immediately on either side of the joint. The wiring also extends directly into each joint, to its electromagnetic brake, from the member to which the joint is rigidly attached. The tethers are configured long enough and flexibly enough (possibly in a wound cord configuration) to allow for significant free movement of the joints.

The electrical wiring of the system connects via the tether connector 127 on the base unit 103 to an electrical connector 243 on the base unit. The electrical connector 243 connects to an electronic control system 245 integrated into a system cart 247. The system cart is further provided with drawers 249 that are configured with one or more compartments with holding devices to conformingly receive and store the multi-joint fixture, and a supply of packaged, unused surgical drapes, and the like, when the device is not in use. Alternatively, the cart could have open compartments behind a cabinet-type door, or even in an open cabinet.

The electronic control system is configured to power and control the electromagnetic brakes. Furthermore, it is configured to do so in response to signals from the electrical switch. More particularly, it is configured to energize the electromagnetic brakes to be locked when the switch forms an electrically closed circuit (i.e., when the switch is released to be in a not-pressed state), and to leave the electromagnetic brakes unlocked when the switch forms an electrically open circuit (i.e., when the switch is in a pressed state). Additionally, the electronic control system is configured to transition the electromagnets from being unlocked to being locked with the application of a non-typical voltage profile to the electromagnetic brakes.

More particularly, the applied voltage profile in the transition includes a first-in-time, transient portion and a second, steady-state portion. The transient portion reaches a transient voltage significantly greater than the steady-state portion voltage, wherein a voltage difference between the transient and steady-state levels is considered significant when it appreciably changes the electromagnet's ability to fully close the gap (between the electromagnet and the draw-plate) and thereby lock the joint (i.e., it appreciably changes the likelihood of the gap closing). Typical anticipated values include that the transient level is approximately twice the steady-state level, and that the transient level is significantly greater than the steady-state level.

While assembled with a surgical drape, the actuation of the electrical switch of this embodiment occurs indirectly and physically through the use of manual actuators, namely the surgical-instrument switch actuator and/or the headpiece switch actuator. Alternative variations of this embodiment can be configured with electrical actuators, i.e. electrical switches on the surgical drape headpiece and the surgical-instrument adapter. In such variations, the surgical drape headpiece would require electrical contacts that extend on both sides of the base plate to provide electrical communication through the sterile barrier provided by the surgical drape. The headpiece and/or fixture connector may also include shielding to prevent interaction with other operating room systems.

Additionally, alternative variations of this embodiment can be configured with electromagnetic actuators, i.e. the communication of switch signals through the surgical drape sterile barrier via electromagnetic fields. In such variations, a field could be intermittently generated on one side of the sterile barrier and its presence (or lack thereof) could be sensed on the other side of the sterile barrier to communicate a switch signal. Likewise, a field generated on one side of the sterile barrier could be manipulated by moving conductors on the other side of the sterile barrier to communicate a switch signal. The headpiece and/or fixture connector may also include shielding to prevent interaction with other operating room systems.

Furthermore, alternative variations of this embodiment can be configured with a headpiece having an actuator that extends in reach of the surgical instrument even while the surgical instrument is attached to the headpiece. In this variation a surgical-instrument switch actuator is not necessary (though it still might be desirable). Moreover, the surgical-instrument connector could be integral with the headpiece.

Figure 10:
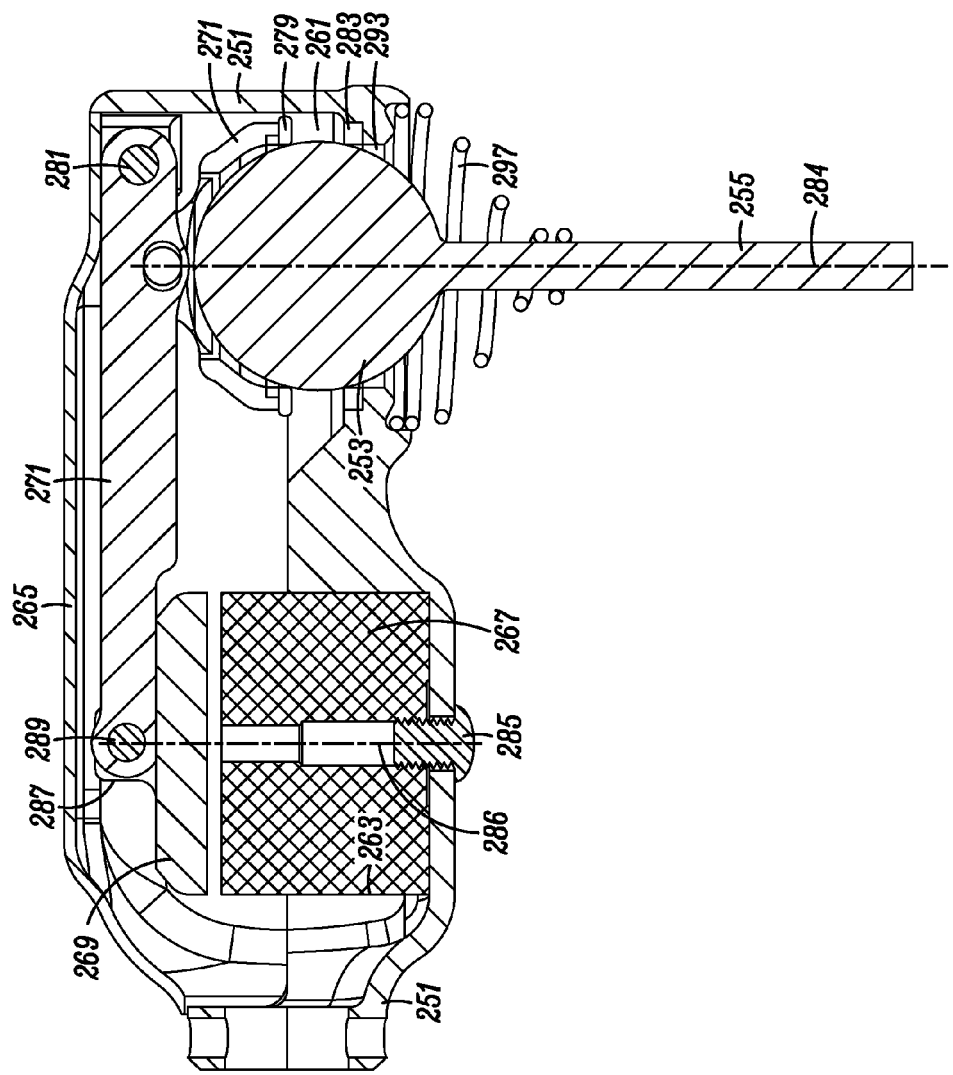
FIG. 10. is a front cross-section view of a second embodiment of a ball joint that could be used in the multi-joint fixture depicted in FIG. 1.

A second embodiment of the invention is configured similar to the first embodiment, except for the second and third ball joints, which have an offset (and levered) configuration. More particularly, with reference to FIG. 10, each of the offset ball joints includes a primary housing 251, a ball, a ball-centering mechanism of the type described for the first embodiment, and an electromagnetic brake mechanism. The outer housing is affixed to or unitary with the rigidly attached member for that ball joint. More particularly, the outer housing of the second ball joint is affixed to or unitary with the first arm, and the outer housing of the third ball joint is affixed to or unitary with the second arm.

Similar to the first embodiment, the ball includes a spherical portion 253 and a shaft 255. The shaft extends from a proximal end at the spherical portion to a distal end, the distal end serving as an attachment point for the connected member. The ball joint defines a ball longitudinal axis that forms a neutral position for the ball and the centering mechanism. As in the first embodiment, the second ball joint is configured with its ball longitudinal axis perpendicular to the general directions of both its attached member and its connected member, and the third ball joint is configured with its ball longitudinal axis perpendicular to the general direction of its attached member, but aligned with and passing through the center of its connecting member (the fixture hub).

Unlike the first embodiment, this particular embodiment is not equipped with a removable inner housing. Instead, the primary housing 251 reacts all housing loads. The primary housing forms a tub-like structure defining a ball cavity 261 in the bottom of the tub and concentric with the ball longitudinal axis, a magnet cavity 263 in the bottom of the tub and concentric with an electromagnet longitudinal axis, and an open top that is covered by a housing cover 265. The electromagnet longitudinal axis is parallel to and offset from the ball longitudinal axis.

The electromagnetic brake is comprised of an electromagnet 267, a draw-plate 269, a lever arm 271, a thrust-cup 277, and a first hardened ring 279. The primary housing 251 is provided with a reaction joint 281 and a second hardened ring 283. Each hardened ring is characterized by a central axis that is concentric with and parallel to the ball longitudinal axis.

A screw 285 is inserted through the primary housing 251 to be threadedly received in the electromagnet 267 along the electromagnet longitudinal axis, thereby holding the electromagnet rigidly with respect to the primary housing. The lever arm 271 holds the draw-plate 269 spaced from the electromagnet along the electromagnet longitudinal axis at a distance creating a small gap normal to the longitudinal axis. The draw-plate includes a post 287 defining a hole for a pin 289 that connects the draw-plate to the lever arm, but allows the lever arm to rotate with respect to the draw-plate. The lever arm extends laterally between the ball longitudinal axis and the electromagnet longitudinal axis, connecting the draw-plate to the thrust-cup 277.

The primary housing reaction joint is located such that the lever arm acts as a lever, with the thrust-cup acting as its fulcrum, to pull the draw-plate 269 away from the electromagnet 267 and establish the gap between the draw-plate and the electromagnet.

The primary housing 251 contains a substantial part of the ball, and the shaft 255 extends out from an orifice 293 of the primary housing. The first and second hardened rings 279 & 283 have diameters smaller than the diameter of the spherical portion 253 of the ball. They are concentrically located along the ball longitudinal axis on longitudinally opposite sides of the center of the spherical portion, and are in contact with the spherical portion. The thrust cup 277 is configured to drive the first hardened ring along the ball longitudinal axis toward the second hardened ring to hold the spherical portion in place and frictionally resist its rotational movement.

Advantageously, the lever arm can be preloaded, thereby incorporating the functions of the keel and the Belleville washer of the first embodiment. More particularly, the draw-plate 269 can be preloaded from above such that the lever arm is configured to form relaxed-state reaction forces between the thrust cup and the draw-plate. The relaxed-state reaction force on the thrust cup drives the first hardened ring towards the second hardened ring and against the spherical portion of the ball. These components are configured such that the relaxed state reaction force on the thrust cup drives the first hardened ring towards the second hardened ring with the proper amount of force to establish the joint rigidity of the ball joint, and thus the presence of the relaxed-state reaction force establishes the unlocked state of the ball joint.

The relaxed-state reaction force draws the draw-plate 269 away from the electromagnet 267 and maintains the gap. The configuration of the reaction joint and the lever arm provides a four to one leverage ratio. Thus, the longitudinal force between the thrust-cup and the lever arm is four times the longitudinal force between the lever arm and the draw-plate (i.e., the electromagnet force is leveraged to a higher value). When the electromagnet is not energized, there are no system forces drawing the draw-plate toward the electromagnet against the pull of the lever arms.

As in the first embodiment, the electromagnet 267 is not energized when the switch is actuated to the actuated position. When the switch is released, a spring bias actuates the switch to a free position, which causes the electromagnet to be energized. The energized electromagnet draws the draw-plate 269 toward the electromagnet to close the gap. The drawn-down draw-plate reacts the lever arm against the reaction joint to push on the thrust-cup. Because of the four to one leverage of the lever arm, the thrust-cup is pushed with four times as much force as the draw-plate is pulled down by the electromagnet.

This energized-state reaction force on the thrust cup drives the first hardened ring 279 towards the second hardened ring 283 and against the spherical portion of the ball to statically hold the spherical portion of the ball and lock the ball joint from any rotational movement, thereby firmly holding the members that the joint connects in a substantially rigid relationship. The presence of the energized-state reaction force establishes the locked state of the ball joint.

Thus, each offset ball joint has an electromagnetic brake mechanism configured to switch between locked and unlocked states, wherein the orientation of the ball within the body is statically held when the brake mechanism is in the locked state, and wherein the application or removal of electrical energy switches the brake mechanism between the locked and unlocked states.

As in the first embodiment, each offset ball joint is further configured with a retaining cap and a spring 297 spiraling in three dimensions to form a centering mechanism that laterally reacts against the shaft 255 so as to drive it laterally back toward the longitudinal axis when it is not already there. The spring is received in a circular groove that is cut into the orifice, and may be held at there by a retainer. Optionally, the spring may be preloaded such that it axially pulls the shaft away from the third housing portion, thus preloading the spherical portion of the ball against the third hardened ring, and thereby contributing to the joint rigidity of the ball joint. Furthermore, the spring may optionally be affixed to the shaft so as to react against rotation of the shaft.

The offset ball joint of this second embodiment is of an offset configuration in that its actuation elements (e.g., an electromagnet, and a draw-plate that establishes a closable gap with the electromagnet) and its braking elements (e.g., a plurality of hardened ring brake elements on opposing sides of the ball) extend and act along two separate, offset and parallel longitudinal axes. It is also of a levered configuration, in that the lever arm provides a four to one mechanical advantage, allowing for a smaller electromagnet to be used.

If the primary housing is rigidly attached to (or unitary with) an arm, the offset configuration of this joint provides a simple way for the masses of the housing, the electromagnetic brake mechanism (e.g., the electromagnet and draw-plate), and the spherical portion of the ball to all be placed substantially along a longitudinal arm axis (i.e., an axis generally defined by the extent of the arm from its proximal to its distal end), while the ball shaft extends perpendicular to the longitudinal arm axis. The configuration of the resulting jointed arm minimizes arm inertia and balances the arm, while providing the fixture with significant configuration flexibility.

The first two embodiments are examples of linear and offset fixtures, both being levered, and both being characterized by a failsafe unlocked configuration. More particularly, the electromagnetic brakes of each joint are locked by the application of electrical energy. If there should be a system failure, such as the loss of electrical power, the electromagnetic brakes would promptly unlock. Further embodiments are envisioned having linear or offset fixtures, characterized by a failsafe unlocked configuration, but not being levered.

Some additional embodiments of fixtures are characterized by a failsafe locked configuration. For example, a third embodiment of the invention (which is provided in a more conceptual state) is configured similar to the first embodiment, except that the ball joints are characterized by a failsafe locked configuration.

Figure 11:
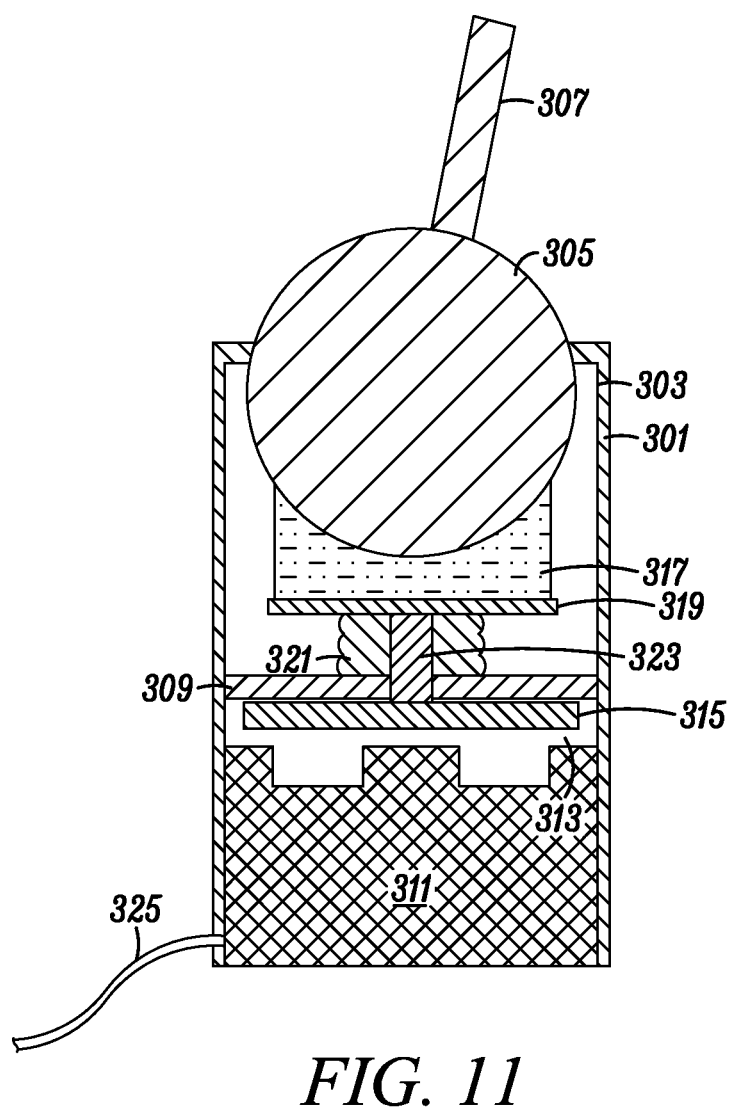
FIG. 11. is a system diagram of a third embodiment of a ball joint that could be used in the multi-joint fixture depicted in FIG. 1.

More particularly, with reference to FIG. 11, each ball joint is an assembly that includes a housing 301 constructed to form an annulus 303 characterized by a diameter less than the overall diameter of a spherical portion 305 of the ball, such that the spherical portion of the ball is retained within the housing. The housing annulus 303 allows the movement of a shaft 307 that extends from the spherical portion 305 of the ball about the center of rotation of the spherical portion.

The housing includes a base plate 309 that is composed of a non-magnetic material. Although not necessary, it may be convenient for the housing base plate to be fastened to the remainder of the housing via a threaded means, thereby allowing adjustability in relative position of these two members. The base plate 309 is maintained in fixed position relative to an electromagnet 311 such that an air gap 313 is formed between a face of the electromagnet 311 and a magnetic draw-plate 315 when the electromagnet 311 is not energized.

A braking member 317 is positioned between the spherical portion of the ball 305 and the base plate 309 generally opposite the region where the ball contacts the annulus 303 of the housing 301. A drive plate 319 is positioned between the braking member 317 and the base plate 309, contacting a face of the braking member 317 opposite that which contacts the spherical portion 305 of the ball. An elastic member 321 is positioned between the drive plate 319 and the base plate 309, contacting a face of the drive plate 319 opposite the face that contacts the braking member 317.

The drive plate 319 is fixed to a connecting rod 323 which passes through clearance holes in the elastic member 321 and base plate 309, and fastens to the magnetic draw-plate 315. When the electromagnet 311 is not energized, the housing 301 and base plate 309 are configured such that an initial compression of the elastic member 321 creates sufficient normal force between the braking member 317 and the spherical portion 305 of the ball to maintain the relative positioning of the assembly (i.e., the position of the shaft 307 with respect to the housing 301), even in the presence of additional loads to the shaft 307.

When current is passed through a wire 325 leading to the electromagnet 311, it energizes the electromagnet, and an attractive magnetic force is created which draws the magnetic draw-plate 315 towards the face of the electromagnet 311 thus reducing or eliminating the air gap 313. The relative translation of the electromagnet 311 and the magnetic draw-plate 315 results in an equidistant translation of the drive plate 319 towards the base plate 309 and away from the annulus 303 of the housing 301. The translation of the drive plate 319 towards the base plate 309 results in additional compression of the elastic member 321 relative to the base plate 309, thereby reducing the normal load between the spherical portion 305 of the ball and the braking member 317. Inclusion of an additional elastic member between the drive plate 319 and the braking member 317 can maintain a predetermined force on the braking member to allow a nominal resistance to motion (i.e., some joint rigidity) even after the electromagnet is energized.

This third embodiment is an example of a fixture characterized by a failsafe locked configuration, and uses joints that lack a levered configuration to leverage the applied braking force to a higher value than that actually generated by their magnets. Other failsafe, locked joint configurations, such as offset configurations and/or levered configurations are also envisioned.

While the first and third and embodiments were described as fixtures having a single type of ball joint, the second embodiment was described as having a first ball joint in a linear, levered, failsafe unlocked configuration, and a second and third ball joint in an offset, levered, failsafe unlocked configuration. Embodiments having other combinations of ball joints are also envisioned. For example, it is envisioned that a multi-joint fixture could have a first ball joint characterized by a failsafe locked configuration, and second and third ball joints characterized by a failsafe unlocked configuration.

The switching system of the present invention provides significant ease-of-use for medical practitioner and is also envisioned for use with other types of fixtures, such as pneumatically activated arms. Additionally, the use of the switching system, drape system and/or electromagnetically driven locking mechanism of the present invention could be applied to other technologies that may rely on mechanical means to lock ball joints, such as a fixture comprising a series of connected ball joints with a common cable passing through them, the fixture being configured to become fixed when the cable is tightened via a threaded mechanism.

It is to be understood that the invention comprises complete surgical device holding systems, multi-joint fixtures, multi-joint fixture control systems, ball joints, switching systems, surgical drapes, surgical-instrument connection systems, surgical instruments, and methods for making and using the same. Additionally, the various embodiments of the invention can incorporate various combinations of these features. In short, the above disclosed features can be combined in a wide variety of configurations within the anticipated scope of the invention.

Furthermore, embodiments of the invention can incorporate various combinations of the apparatus described in provisional Application No. 60/810,265, filed Jun. 1, 2006, which is incorporated herein by reference for all purposes.

While particular forms of the invention have been illustrated and described, it will be apparent that various modifications can be made without departing from the spirit and scope of the invention. Thus, although the invention has been described in detail with reference only to the described embodiments, those having ordinary skill in the art will appreciate that various modifications can be made without departing from the scope of the invention. Accordingly, the invention is not intended to be limited by the above discussion, and is defined with reference to the following claims.

What is claimed is:

1. A system for holding an instrument, comprising:
   a base unit;
   a hub configured to detachably hold the instrument;
   a group of one or more arms serially connected by a plurality of joints between the base unit and the hub, one or more of the plurality of joints being a ball joint, including, a ball, a body containing a portion of the ball, a brake element, and an electromagnetic brake mechanism configured to actuate the brake element between a locked state wherein the brake element presses against the ball with a force adequate to fix the orientation of the ball, and an unlocked state wherein the brake element does not press against the ball with a force as high as that of the locked state;
   a control system configured to actuate the electromagnetic brake mechanism with a voltage profile characterized by a first, transient portion and a second, steady-state portion, the transient portion voltage being significantly greater than the steady-state portion voltage; and
   a system cart, wherein, the system cart houses the control system and one or more storage compartments configured to house the group of one or more arms serially connected by the plurality of joints when not in use.

2. The system for holding an instrument of claim 1, wherein in the unlocked state, the brake element presses against the ball with a force that is less than that of the locked state.

3. The multi-joint fixture of claim 2, and further comprising a switch carried proximate the hub, the switch being configured to control actuation of the electromagnetic brake mechanism.

4. The system for holding an instrument of claim 1, wherein the electromagnetic brake mechanism is only configured to actuate the brake mechanism to the locked state when the system is powered.

5. The system for holding an instrument of claim 2, wherein the brake mechanism includes a brake element, a driver configured to actuate the brake element, and a lever arm connecting the driver to the brake element, and being configured to use leverage to react against the brake element with a greater force than against the driver.

6. The system for holding an instrument of claim 1, wherein one or more of the joints of the plurality of joints include a centering mechanism configured to bias the joint toward a neutral position.

7. The system for holding an instrument of claim 1, and further comprising:
   a switch carried proximate the hub, the switch being configured to control actuation of brake mechanism.

8. The multi-joint fixture of claim 7, wherein every joint has a brake mechanism configured to lock the orientation of the joint when the brake mechanism is actuated, and wherein the switch controls actuation of the brake mechanism of each joint.

* * * * *